(12) United States Patent
Missotten et al.

(10) Patent No.: US 8,218,912 B2
(45) Date of Patent: Jul. 10, 2012

(54) METHOD AND APPARATUS FOR DETECTING ERRORS IN ELECTRONICALLY PROCESSED IMAGES

(75) Inventors: Bart M. A. Missotten, Winksele (BE); Carmen S. Wallays, Izegem (BE)

(73) Assignee: CNH America LLC, New Holland, PA (US)

( * ) Notice: Subject to any disclaimer, the term of this patent is extended or adjusted under 35 U.S.C. 154(b) by 938 days.

(21) Appl. No.: 12/283,549

(22) Filed: Sep. 12, 2008

(65) Prior Publication Data
US 2009/0074243 A1 Mar. 19, 2009

(30) Foreign Application Priority Data
Sep. 14, 2007 (GB) .................................. 0717986.4

(51) Int. Cl.
*G06K 9/03* (2006.01)

(52) U.S. Cl. ...................................... 382/309; 382/190

(58) Field of Classification Search .................. None
See application file for complete search history.

(56) References Cited

U.S. PATENT DOCUMENTS
6,829,727 B1 * 12/2004 Pawloski .................... 714/28
7,602,985 B2 * 10/2009 Gao et al. .................. 382/240

FOREIGN PATENT DOCUMENTS
| EP | 826959 A1 * | 3/1998 |
| JP | 2003289712 | 10/2003 |
| JP | 2007189369 | 7/2007 |
| WO | WO 2006010761 | 7/2004 |

OTHER PUBLICATIONS
G.J. Hay, K.O. Niernann, D.G. Goodenough, "Spatial Thresholds, Image-Objects, and Upscaling: A Multiscale Evaluation", Oct. 1997, Remote Sensing of Environment, vol. 62, Issue 1, pp. 1-19.*

* cited by examiner

*Primary Examiner* — Jason M Repko
*Assistant Examiner* — Siamak Harandi
(74) *Attorney, Agent, or Firm* — Michael G. Harms

(57) ABSTRACT

A method of detecting one or more errors in a series of electronically processed, multi-pixel images, the pixels of which correspond from one image to the next, the method including monitoring the reflectance of one or more of the corresponding pixels during sequential processing of each image of the series and, if the reflectance value of a pixel is invariant or substantially invariant in more than a predetermined number of consecutive said images, and identifying an error.

11 Claims, 3 Drawing Sheets

METHOD AND APPARATUS FOR DETECTING ERRORS IN ELECTRONICALLY PROCESSED IMAGES

CROSS REFERENCE TO RELATED APPLICATIONS

This Patent Application claims priority under 35 U.S.C. §119 to GB 0717986.4, filed on Sep. 14, 2007 titled, "A Method and Apparatus for Detecting Errors in Electronically Processed Images" and having Bart M. A. Missotten and Carmen S. Wallays as inventors. The full disclosure of GB 0717986.4 is hereby fully incorporated herein by reference.

This invention relates to a method and apparatus for detecting errors in electronically processed images.

Image processing increasingly forms an important aspect of many industrial processes. It is commonly required to monitor the conditions of products, chemicals, minerals, crops and all manner of other commodities that pass through processing apparatuses normally out of sight of human operators.

Such monitoring can of course take the form of the generation of visible images that are displayed eg. to a machine operator such that he can intervene in the industrial process in the event of noticing some abnormality.

Additionally image processing increasingly takes the form of the generation of digital images from which eg. processed data may be extracted electronically.

One example of this occurs in the crop movement path of a crop harvesting machine such as a combine harvester. The invention relates primarily to such a usage of image processing technology, although it is equally validly applicable in a very wide range of other image processing scenarios such as but not limited to the ones indicated above.

A combine harvester is a complex machine that incorporates numerous movement paths for crop and materials associated with or generated by a harvesting operation.

It is often desirable to monitor the flow of crop in such movement paths, for example for the purpose of assessing whether the harvesting machine is operating correctly.

At its simplest, such monitoring may take the form of providing a video camera that projects an image to an operator in the cab of the vehicle.

Such a form of image-based monitoring of process quality, however, is distinctly sub-optimal for various reasons. The main one of these is that at any given location in eg a crop movement path the conditions are, during use of the harvesting machine, changing extremely rapidly. It is almost inconceivable that the operator of such a machine could reliably draw conclusions from the mere visual interpretation of crop images, even if it were not additionally a requirement that he pay close attention to all aspects of the setting of the harvesting machine such as the forward speed, the direction of movement, the transmission ratio, the header bar setting and the settings of various internal components.

Furthermore, certain undesirable conditions that can arise in the crop movement path of a combine harvester simply do not lend themselves readily to being identified using a process of visual inspection by a human operator.

One example (of several possible situations) relates to the occurrence of "material other than grain" or MOG in crop conveyed through and processed by a combine harvester.

It is becoming increasingly important to assess the percentage of MOG in crop being harvested.

This is partly because for economic reasons it is undesirable for crop in the grain tank of a combine harvester to contain anything other than a minimal percentage of MOG.

Perhaps more importantly, however, it has been found that assessing the level of MOG can give rise to important variables that when used to generate electronic signals may be used to improve the accuracy of control of the harvesting machine.

For many years it has been recognised that even small percentage improvements in the overall efficiency of harvesting machines are economically desirable. As a result, therefore, apparatuses have been devised whose purpose is to assess the instantaneously prevailing average MOG content in crop being processed in a combine harvester.

The typical form of such apparatus includes a camera (such as a CCD-TV or other camera that is capable of producing digital images), an illumination system including a timed output lamp; and a (typically, programmable) processing device that is capable of processing images of the crop at a predetermined location in the crop movement path and deriving useful data therefrom.

As is well known, during harvesting operations crop moves continuously through a combine harvester. Apparatus such as that outlined hereinabove for capturing and processing digital images typically produces a series of images at regular intervals. One per se known MOG-detecting imaging system produces between 1 and 10 images per second (depending on the precise set-up of the apparatus). Inherently, as a result of the continuous movement of the crop within the harvesting machine, each of these images differs from the immediately preceding one. The purpose of the programmable device therefore is, in such a case, to establish average levels of MOG.

Typically in an image-based MOG assessment system of a combine harvester a glass or other translucent material window is provided for the purpose of protecting the camera while permitting it to capture images according to the aforesaid sequential or series-based regime.

MOG may include various components such as straw, chaff, broken kernels, dirt, leaf parts, insects, weed seeds and even small stones that may be ingested into the harvesting machine together with the desired parts of the crop from which valuable grains are separated according to a threshing process that is per se well known.

It is in the nature of MOG therefore that particles of it may become adhered to the window. This is especially true if, for example, the MOG includes leaf or stem parts and has a high moisture content thereby rendering such parts sticky. Additionally if the dust or dirt content of the MOG is high and moisture is present in the crop movement path adjacent the window this can give rise to the creation of a mud or paste that can attach to and obscure part of the window.

Obscuring of part of the window can lead to spuriously high MOG content indications. If the MOG percentage is either assessed visually by a combine harvester driver or is used as an input variable for the purpose of eg. providing an indication of the overall quality of the output of the harvesting machine the presence of MOG adhered to a camera window can be strongly undesirable.

Furthermore under circumstances as described above the amount of MOG adhered to the window is likely to increase over time while the (typically high moisture) conditions that cause adherence of MOG prevail. This can result in significant levels of noise in the image signals that are to be processed by the programmable device. This can of course affect the overall accuracy of control of the harvesting machine.

It follows from the foregoing that there is a need for a control method and apparatus that obviate or ameliorate the effects of adherent MOG on an image processing sub-system of a harvesting machine (or another processing machine such as those described above).

According to the invention therefore there is provided a method of detecting one or more errors in a series of electronically processed, multi-pixel images the pixels of which correspond from one image to the next, the method comprising the steps of:

a) monitoring the reflectance of one or more of the corresponding pixels during sequential processing of each image of the said series and, if the reflectance value of a said pixel is invariant or substantially invariant in more than a predetermined number of consecutive said images, b) identifying an error.

An advantage of this method is that it identifies genuine adherent-MOG errors of the kind that prevail during the generation of several successive images, whilst avoiding alerting etc. on the basis of transient features of an image that, generally speaking, should not be identified as errors.

Conveniently the reflectance is monitored in a predetermined wavelength range, and more particularly in a wavelength range that is centered on 525 nm.

The use of a predetermined, comparatively narrow wavelength range assures consistency of the error identification process. Additionally it has been found through experimentation that the 525 nm wavelength of reflected light is particularly well suited to the identification of errors in materials such as crops conveyed in a crop movement path of a harvesting machine such as a combine harvester. This is because images taken at this wavelength tend to have a greater intensity variation than images at other wavelengths. Preferably the precise range of wavelengths of illumination is 520-530 nm, although when assessing material other than granular crops other wavelength ranges, centred on other wavelength means, may be suitable. When the MOG detector uses images taken in a limited number of wavelengths in the range of 400 to 900 nm, any wavelength in this range may be chosen.

In more detail, the step of monitoring the reflectance preferably includes monitoring the variance $\sigma^2$ or standard deviation $\sigma$ of a reflectance value of one or more said pixels in the series of images. Thus for any particular pixel in each of a series of images an assessment of the variance or the standard deviation is used to establish whether an error condition exists. The utilisation of a variance $\sigma^2$ is computationally advantageous.

In one preferred embodiment of the method of the invention the series of images consists of four successive images of a plurality created at intervals.

Such a sample size is particularly well suited to use of the method in a combine harvester. In other applications of course other numbers of images may be used.

In a preferred aspect the method of the invention includes the steps defined in claims 6-8 hereof. Thus the method of the invention preferably involves creating from a grayscale image an invariant pixel image representing the pixels that have an invariant or substantially invariant reflectance value over the said predetermined number of consecutive said images; and inserting the said invariant pixel image or an outline thereof into one of the images of the series in the location of the invariant pixel to create a modified image.

As indicated in claim 7 invariant pixel image may be generated in a number of advantageous ways, one optional version of which involves the step of creating a grayscale image representing the value of the variance $\sigma^2$ of the reflectance value of the pixels value over the said consecutive images and thresholding the grayscale image so as to generate an invariant pixel image.

The thresholding step may comprise, within the scope of the invention, generating a binary image by the allocation of a logic level '1' to each pixel, in the grayscale image, representing an invariant pixel image. In the preferred embodiment of the method of the invention such pixels are those having a variance or standard deviation value below a threshold value.

Conveniently the method then may include the step of excluding any pixel having a logic level of 1 from further processing during processing of the series of images.

In a further optional refinement of the method of the invention, it is possible to generate an audible, visual or other transmissible alarm signal in the event of the invariant pixel image containing more than a predetermined number of pixels having an invariant or substantially invariant reflectance value.

Conveniently the predetermined number of pixels corresponds to 10% of the total number of pixels in the modified image.

The invention is also considered to reside in apparatus for detecting one or more errors in a series of electronically processed, multi-pixel images the pixels of which correspond from one image to the next, the apparatus including a camera that is capable of generating a said series of images; and a programmable processing device that is programmed to carry out a method as defined hereinabove in respect of the images.

Conveniently the apparatus is configured as part of a crop monitoring device. Even more preferably the crop monitoring device is part of or operatively connected to a crop movement path in a combine harvester.

There now follows a description of preferred embodiments of the invention, by way of non-limiting example, with reference being made to the accompanying drawings in which.

Figure 1:
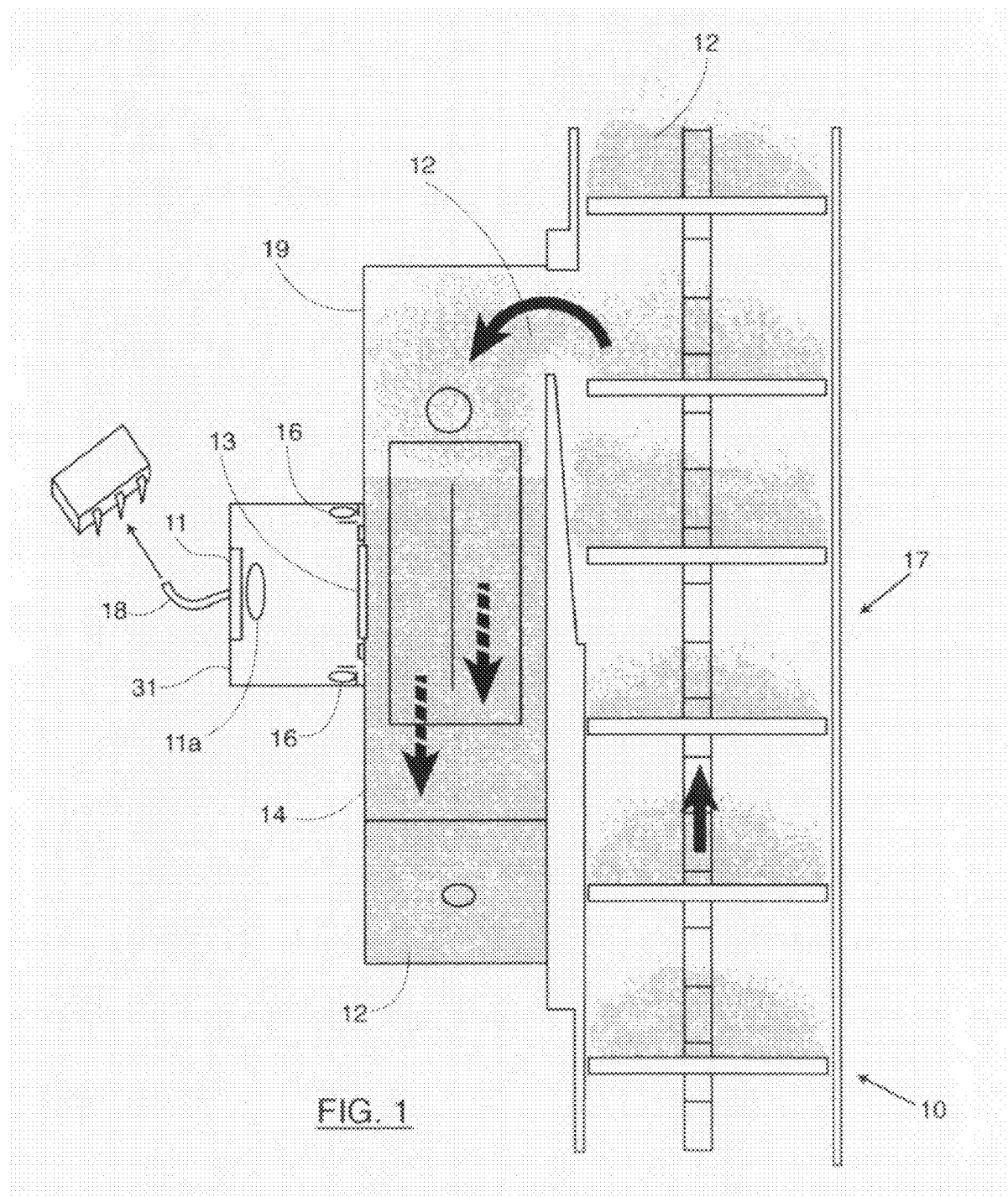
FIG. 1 shows in highly schematic form an apparatus, according to the invention, that may be used for the generation of images in processing machinery such as but not limited to a combine harvester.

Referring to the drawings in FIG. 1 an apparatus 10 comprises a camera 11 that is configured to capture a series of images of material 12 being processed in processing apparatus.

The camera 11 is capable of producing a sequence of digital images.

Camera 11 includes a lens 11a that is trained to capture images of the material 12 by way of light that is incident via a transparent window 13 formed in a bulkhead or wall 14.

Window 13 may be made of glass or another translucent material.

One or more lamps such as but not limited to LEDs 16 may be positioned eg. in the bulkhead for the purpose of sequentially illuminating the material 12 in timed relation to successive image capture operations of the camera 11. In the embodiment shown the LED's transmit light to the rear wall of a cuboidal housing 31 that contains the camera1 11. The light is reflected from the rear wall forwardly via window 13 to illuminate the material 12. Other illumination arrangements are possible within the scope of the invention.

As indicated, in the preferred embodiment of the invention the material 12 is crop being conveyed along a crop movement path represented in FIG. 1 by vertical (paddle-type) conveyor 17. The arrows in FIG. 1 illustrate the crop movement path in the specific embodiment under consideration. Many variants on the movement path of the material 12 are possible.

Other variants on the aforementioned arrangement, within the scope of the invention, include for example that the material 12 need not be crop, or if it is crop it need not be granular. The LEDs may additionally or alternatively be positioned on the opposite side of the housing 31 and their light might be transmitted directly onto the crop 12 through the window 13.

Furthermore, the conveyor 17 may be replaced by any of a wide range of other transporting and processing apparatuses. In the specific case of a combine harvester such apparatuses may include horizontal conveyors of various kinds; and augers.

When the material 12 is grain contained in a harvesting machine MOG may become adhered to the window 13. As described hereinbelow, this may cause noise in any image signals generated by the camera 11 for transmission via eg. cabling 18 or wirelessly to a processing device represented schematically at reference numeral 19. The processing device, which preferably is programmable and is programmed eg. during installing of the apparatus 10, may take any of a very wide range of forms, and may be located anywhere in the processing apparatus or may even be located externally thereof (and indeed externally of the combine harvester). Processing device 19 is shown in FIG. 1 schematically in the form of a chip package.

When MOG adheres to the window 13, errors in data transmitted to the processing device 19 and/or in commands generated thereby (or by a machine operator acting in accordance with images displayed eg. in operator cab or booth), may develop. For reasons explained hereinabove this is undesirable.

However, the effects of adherence of MOG or other (when the material 12 is not, itself, harvested grains) contaminants may be eliminated through practicing the method of the invention. To this end, therefore, the processor 19 is in accordance with the invention programmed to carry out the method steps set out herein.

Figure 2:
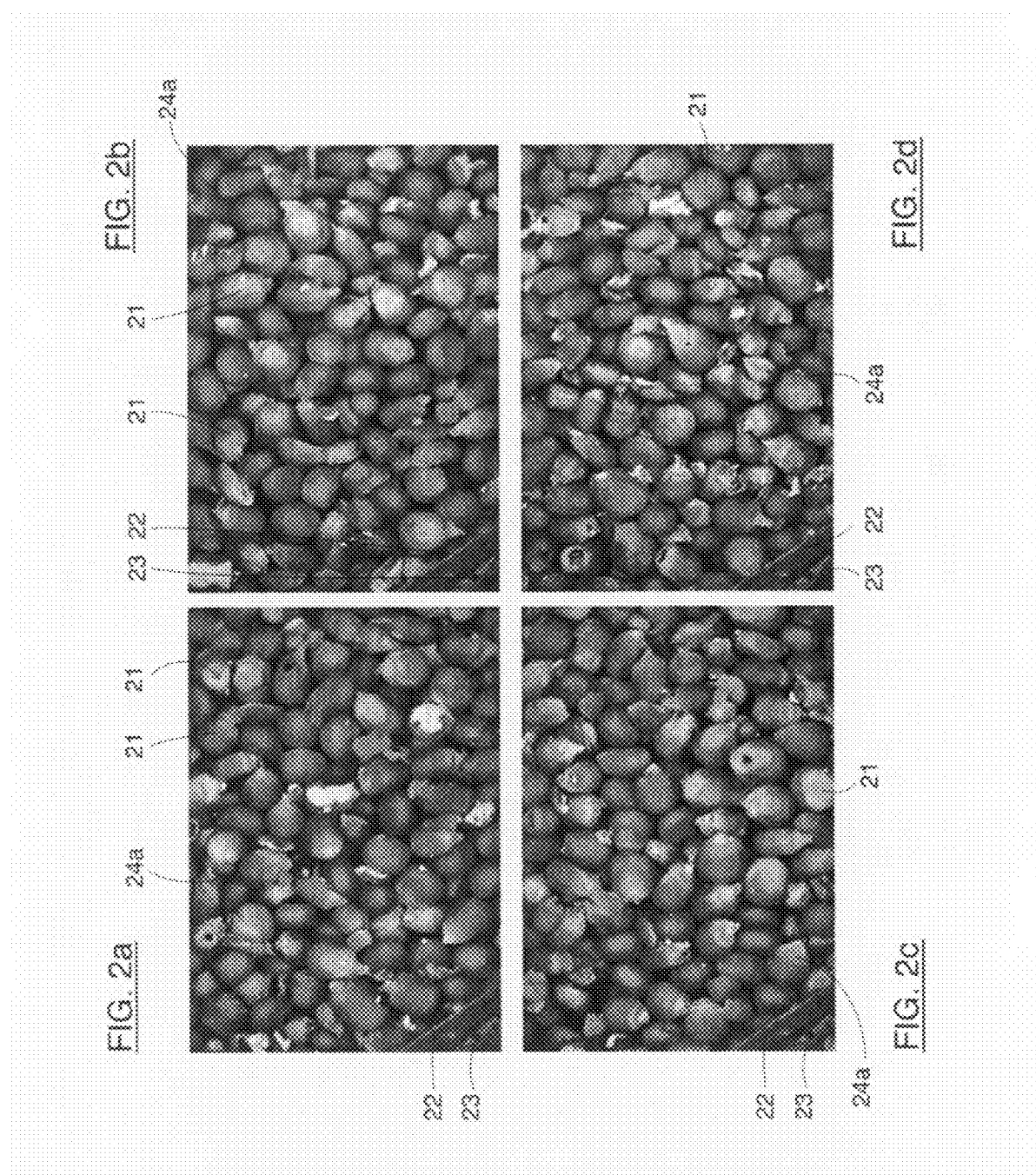
FIGS. 2a, 2b, 2c and 2d show a series of four images that may be generated by apparatus such as that shown in FIG. 1.
Figure 3:
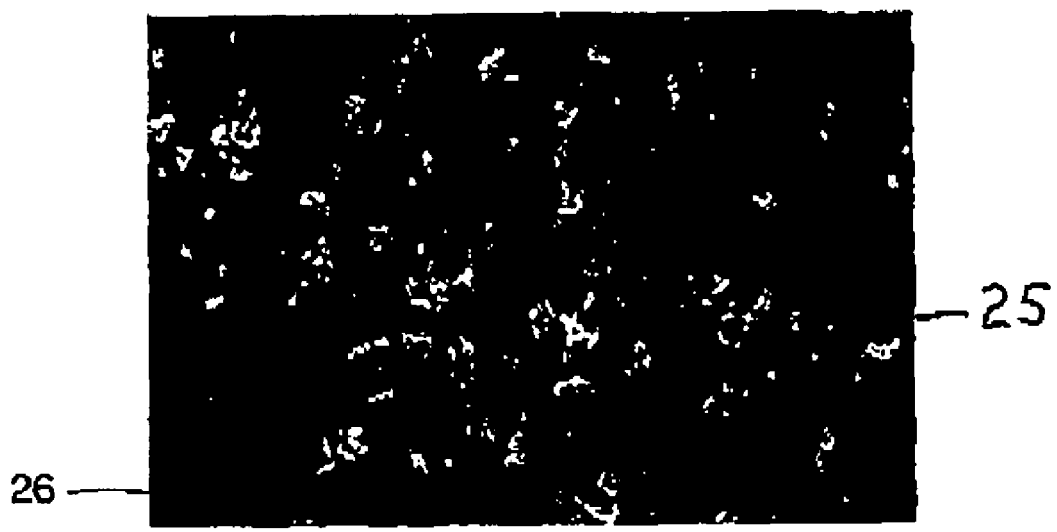
FIG. 3 shows the result of a variance or standard deviation calculation performed on the images of FIG. 2.
Figure 4:
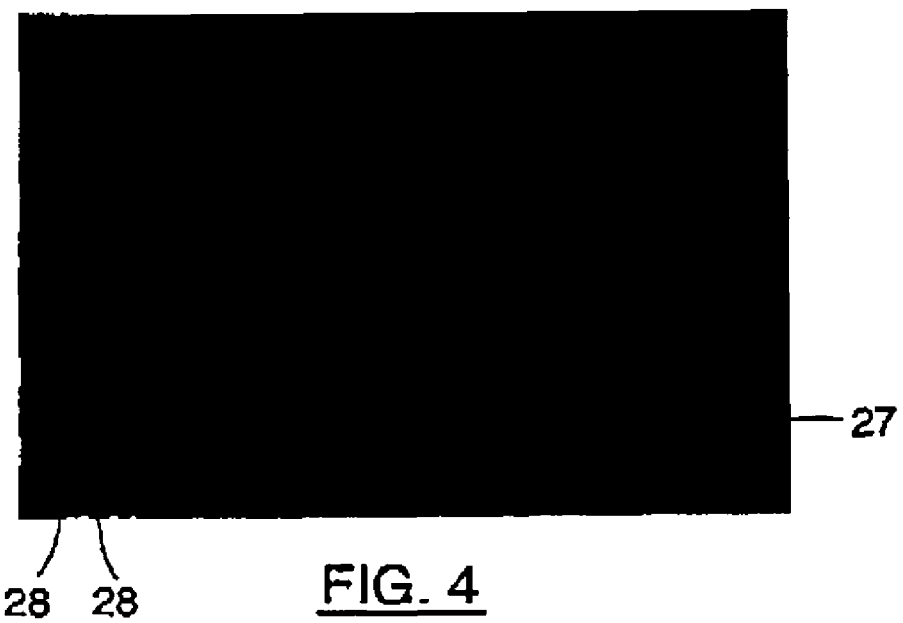
FIG. 4 shows the result of thresholding of the FIG. 3 image, in accordance with the invention.

The result of carrying out the method of the invention is shown progressively in FIGS. 2, 3 and 4.

FIGS. 2a, 2b, 2c and 2d show a series of (in the preferred embodiment) four images 24a of granular crop captured by a camera such as device 11 of FIG. 1 moving in a crop movement path of a combine harvester. The pixels of each image correspond in location, size and shape but their hue, intensity and saturation values change as explained below.

As is evident from FIGS. 2a to 2c, each image is constituted predominantly by grains 21. Since the images are captured at intervals of approximately 4 seconds from one image to the next, the positions, sizes and orientations of the grains vary. In other words, in a normal situation each consecutive image differs from the preceding one by virtue of movement of the grains in the crop movement path.

However, a portion of each of the images of FIGS. 2a to 2d is substantially invariant, being represented by the presence of MOG in the form of straw 22 and chaff 23 particles of which are shown adhered in the bottom left hand corner of the window 13 via which the images are captured by the camera 11.

As explained hereinabove, the presence of invariant parts of the images amounts to noise in the image signals. The noise can reduce the accuracy of eg. any MOG calculation carried out on the material passing along the crop movement path.

Following completion of the method step of calculating the variance $\sigma^2$ of a reflectance value in a predetermined wavelength range (which as noted preferably is 525 nm), the variance for each pixel is represented in a grayscale image 25 shown in FIG. 3. Black areas represent pixels the reflectance of which has not changed or has barely changed from one image to the next. This is typical for images of "blocked" crop portions, i.e. those parts that correspond eg to the presence of adhered MOG. Light areas represent pixels with a highly variable reflectance as caused by the repeated replacement of the crop particles over the series of original images.

In FIG. 3, the plurality of resulting, invariant pixels appears as one or more (depending on the number of MOG particles adhered) dark areas 26 corresponding to the locations of the straw 22 and chaff 23 particles visible in FIGS. 2a to 2d.

Following thresholding of the greyscale image 25 a further modified image 27 is produced, as shown in FIG. 4. In FIG. 4 the regions of the adhered MOG appear as areas 28 of contrasting colour to the remainder of the image.

The threshold may be chosen at a very low level in order to exclude the low variance values following from distinct crop portions that happen to present similar reflectance values at the same pixel in the four images. It is also conceivable, within the scope of the invention, to generate the threshold automatically as a function of the distribution of grey values in the variance image 25.

Following creation of the further modified image 27, it is possible computationally in the processing device 19 to allocate a logic level of eg. 1 to the contrastingly coloured area 28 and a logical level of 0 to the remainder of the further modified image.

Such an allocation can then be used to eliminate the effect of the adhered MOG from the image data that may be used for other purposes in the harvesting machine. Such other purposes include but are not limited to the generation of command signals for controlling settable sub-systems of the harvesting machine. The processing device 19 may be programmed to disregard the pixels having a logic level of 1, such that the system output only takes account of the image areas that show at least some variation over the series of images. This avoids for instance the problem that a stuck MOG particle constantly contributes to a high MOG content value as calculated by the system.

A display may show to the operator the location of the low variance pixels. In an advantageous combination within the scope of the invention, the processing device 19 may derive an outline of the invariant area and display this outline in a contrasting colour on the image of the crop. This allows the operator to assess the nature of the invariant area (MOG, dirt, scratches) and to take appropriate actions. The generation of the outline may take place in accordance with an outlining technique with which the skilled reader will be familiar.

Should the number of pixels in the further modified image 27 having a logic level 1 exceed a predetermined threshold (such as, in the preferred embodiment, 10%) as a further refinement it is possible to generate a warning signal that may be audible, visible, vibratory or a combination of such signals for transmission via an output device located eg. in the operator cab of the combine harvester. The harvesting machine driver, or a control device, can then prompt, take or initiate appropriate remedial action. Such action may for example amount to halting of the harvesting operation and cleaning of adhered MOG from the window 13.

Thus, overall, the method and apparatus of the invention at the most basic level provide for elimination of the signal noise effects of blocked particles, such as MOG, in a combine harvester (or other contaminants in other processing apparatuses). At a greater level of refinement control commands of varying kinds may be generated; and alerts and/or emergency action generated by way of further commands.

The invention claimed is:

1. A method of detecting one or more errors in a series of electronically processed, multi-pixel images the pixels of which correspond from a series of images of a crop movement path of a crop harvesting machine, the method comprising the steps of:

monitoring the reflectance of one or more of the corresponding pixels during sequential processing of each image of the series and, if the reflectance value of the pixel is invariant or substantially invariant in more than a predetermined number of consecutive images, creating a grayscale image representing the value of the variance of a pixel over the series of images;

selecting a reflectance threshold value that is the lowest threshold value from a group of threshold values, the group of threshold values automatically generated as a function of the distribution of gray values in the grayscale image;

thresholding the grayscale image so as to generate an invariant pixel image, representing the pixels, whose reflectance value is invariant or substantially invariant;

inserting the invariant pixel image or an outline thereof into one of the images of the series in the location of the invariant pixel to create a modified image;

allocating a logic level of 1 to each pixel in the modified image representing an invariant pixel image, wherein an invariant pixel image having a logic level of 1 must also be below the reflectance threshold value, and allocating a logic level of 0 to each remaining pixel in the modified image; and generating a command signal for controlling a sub system of the crop harvesting machine based on the allocation of logic levels in the modified image.

2. A method according to claim 1 wherein the reflectance is monitored in a predetermined wavelength range.

3. A method according to claim 2 wherein the predetermined wavelength range is centered on 525 nm.

4. A method according to claim 1 wherein the step of monitoring the reflectance includes monitoring the variance or the standard deviation of a reflectance value of each of the one or more pixels in the series of images.

5. A method according to claim 1 wherein the series includes four successive images of a plurality created at intervals.

6. A method according to claim 1 including the step of excluding any pixel having a logic level of 1, such that only pixel images having a logic level of 0 are further processed to create the modified image.

7. A method according to claim 1 including the step of generating an audible, visual or other transmissible alarm signal in the event of the invariant pixel image containing more than a predetermined number of pixels associated with the logic level of 1.

8. A method according to claim 7 wherein the predetermined number of pixels corresponds to 10% of the total number of pixels in the modified image.

9. Apparatus for detecting one or more errors in a series of electronically processed, multi-pixel images the pixels of which correspond from a series of images of a crop movement path of a crop harvesting machine, the apparatus comprising:

a camera that is capable of generating the series of images; and a programmable processing device that is programmed to monitoring the reflectance of one or more of the corresponding pixels during sequential processing of each image of the series and, if the reflectance value of the pixel is invariant or substantially invariant in more than a predetermined number of consecutive said images, then the device creates a grayscale image representing the value of the variance of a pixel over the series of images, the device selects a reflectance threshold value that is the lowest threshold value from a group of threshold values, the group of threshold values automatically generated as a function of the distribution of gray values in the grayscale image, the device thresholds the grayscale image so as to generate an invariant pixel image, representing the pixels, whose reflectance value is invariant or substantially invariant, the device inserts the invariant pixel image or an outline thereof into one of the images of the series in the location of the invariant pixel to create a modified image, the device allocates a logic level of 1 to each pixel in the modified image representing an invariant pixel image, wherein an invariant pixel image having a logic level of 1 must also be below the reflectance threshold value, the device then allocates a logic level of 0 to each remaining pixel in the modified image and the device generates a command signal for controlling a sub system of the crop harvesting machine based on the allocation of logic levels in the modified image.

10. Apparatus according to claim 9 wherein the crop monitoring device is configured as part of a crop monitoring device.

11. Apparatus according to claim 10 wherein the crop monitoring device is part of or operatively connected to a crop movement path in a combine harvester.

* * * * *